United States Patent [19]

Yamanaka et al.

[11] Patent Number: 5,278,012
[45] Date of Patent: Jan. 11, 1994

[54] METHOD FOR PRODUCING THIN FILM MULTILAYER SUBSTRATE, AND METHOD AND APPARATUS FOR DETECTING CIRCUIT CONDUCTOR PATTERN OF THE SUBSTRATE

[75] Inventors: Chie Yamanaka; Toshiaki Ichinose, both of Yokohama; Takanori Ninomiya, Hiratsuka; Hisafumi Iwata, Yokohama; Yasuo Nakagawa, Chigasaki; Nobuyuki Akiyama, Yokohama, all of Japan

[73] Assignee: Hitachi, Ltd., Tokyo, Japan

[21] Appl. No.: 938,516

[22] Filed: Sep. 2, 1992

Related U.S. Application Data

[63] Continuation of Ser. No. 499,812, Mar. 27, 1990, abandoned.

[30] Foreign Application Priority Data

Mar. 29, 1989 [JP] Japan .................................. 1-075114

[51] Int. Cl.$^5$ ..................... G01N 21/88; G01N 21/64
[52] U.S. Cl. ...................................... 430/30; 430/311; 250/562; 250/563; 356/237
[58] Field of Search ............... 430/30, 311, 313, 314, 430/315, 322, 323, 324, 331; 250/562, 563; 356/237

[56] References Cited

U.S. PATENT DOCUMENTS

| | | | |
|---|---|---|---|
| 4,538,909 | 9/1985 | Bible et al. | 356/327 |
| 4,816,686 | 3/1989 | Hara et al. | 356/327 |
| 4,999,511 | 3/1991 | Kohno | 356/327 |

FOREIGN PATENT DOCUMENTS

| | | | |
|---|---|---|---|
| 1-10249 | 1/1989 | Japan | 430/30 |
| 2-266357 | 10/1990 | Japan | 430/30 |

Primary Examiner—Marion E. McCamish
Assistant Examiner—Kathleen Duda
Attorney, Agent, or Firm—Antonelli, Terry, Stout & Kraus

[57] ABSTRACT

A method for producing a thin film multilayer substrate having a base substrate, and, which a plurality of conductor pattern layers superposed thereon through dielectric layers therebetween comprises the steps of: optically detecting the uppermost conductor pattern layer whenever the conductor pattern layer is formed on the base substrate; inspecting an absence and/or presence of a fault of the conductor pattern layer; and repairing a faulty portion in accordance with fault position data detected by the inspecting. According to this method, it is possible to enhance a production yield of relatively large size of thin film multilayer substrates which needs a relatively small amount of production at a high production cost, for mounting LSI chips thereon.

23 Claims, 16 Drawing Sheets

F I G. 10
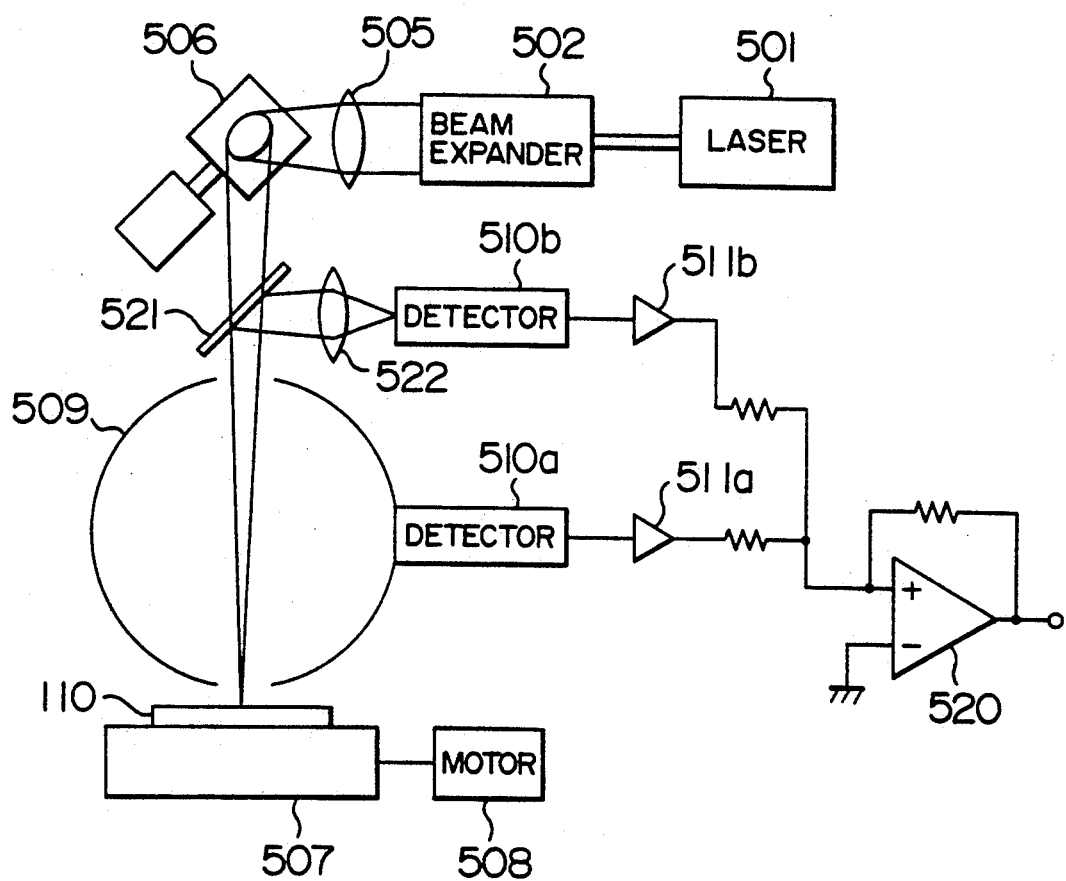

F I G. 11
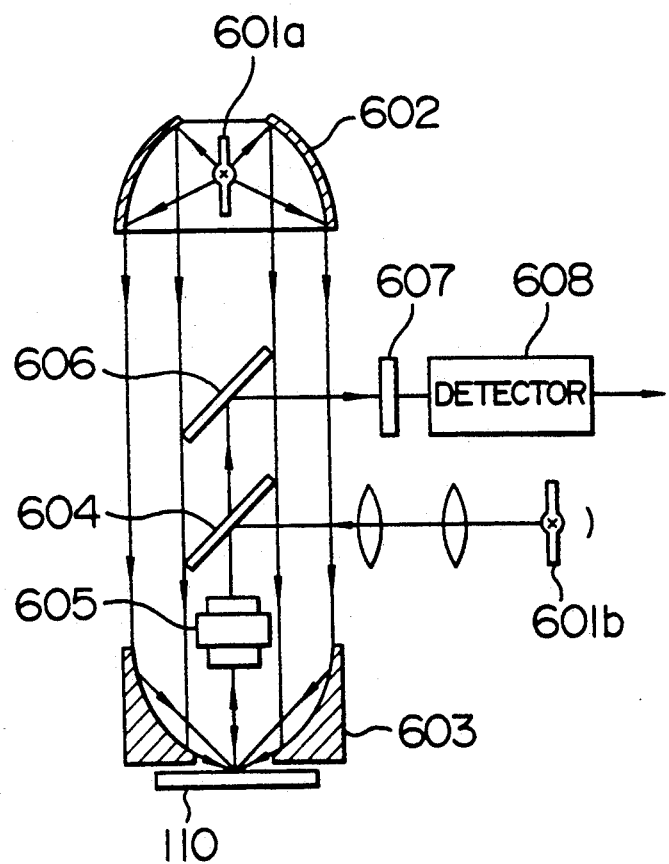

METHOD FOR PRODUCING THIN FILM MULTILAYER SUBSTRATE, AND METHOD AND APPARATUS FOR DETECTING CIRCUIT CONDUCTOR PATTERN OF THE SUBSTRATE

This application is a continuation application of Ser. No. 07/499,812, filed Mar. 27, 1990 now abandoned.

BACKGROUND OF THE INVENTION

The present invention relates to a method for producing a thin film multilayer substrate or multilayer circuit board which is made by superposing a plurality of conductor pattern layers through dielectric or insulating layers interposed between the conductor pattern layers, and more particularly to a method for producing a thin film multilayer substrate by depositing thin film multilayer conductor patterns on a substrate for mounting LSI chips and the like in an electronic computer or the like.

The present invention relates also to a conductor pattern detecting method which is available for inspection of a configuration of an uppermost conductor pattern of a thin film multilayer conductors superposed alternatingly with dielectric or insulating layers, and it relates to an apparatus therefor.

A technique for using a polyimide resin having a low dielectric constant and a high heat resistance as an insulating layer of a thin film multilayer substrate for mounting LSI chips and the like at a high mounting density is shown in, for example, NEC Technical Report 39, No. 1 (1986), pages 36-41.

Such a technique is also disclosed in NIKKEI MICRODEVICES, January 1988, pages 70 to 77.

However, since this technique is relatively new, only NIKKEI MICRODEVICES, January 1988 shows an outline of a production method, and the prior art fails to show a specific step for inspection of faults of the product during a production process and other steps.

On the other hand, an inspection step of a conductor pattern in a manufacturing process of a thin film multilayer substrate including a semiconductor wafer for LSIs and the like is disclosed in, for example, Japanese Patent Unexamined Publication No. 57-208153. In addition, a technique for inspecting how the pattern has been produced, by using a line width measuring device, is shown in Precision Engineering Association's monthly report 54/4/1988, pages 34 to 38 entitled "TECHNIQUE FOR MEASURING FINE DIMENSION OF WAFER." However, these techniques disclosed in these printed publications are used for checking the manufacturing process of the multilayer substrate and the like and for controlling the condition of the manufacturing process to keep the manufacturing process itself at an optimum condition, by monitoring a pattern formed on a midway of the manufacturing process. The faulty chips and the like which were picked up in the inspection step were finally disposed.

Namely, the above-described prior art inspection methods are available for producing a large amounts of products by using silicon wafers such as LSI chips but are not intended to produce a small amount of products which need a high cost per one product, as in a step for forming a thin film multilayer circuit conductor pattern on a ceramic substrate.

Incidentally, the above-described Japanese Patent Unexamined Publication 57-208153 discloses a method in which, in order to inspect the configuration of a circuit conductor pattern of an uppermost layer of a thin film multilayer circuit conductors superposed alternatingly with insulating films and circuit conductor patterns, a downward or bright field illumination light and a dark field illumination light are simultaneously projected to brightly sense the uppermost layer of circuit conductor pattern irrespective of stepped portions and flat portions thereof, whereby an aluminum circuit conductor pattern of the uppermost layers of the multilayer patterns of the LSI wafer is visualized for detection. However, in this case, it is assumed that only one aluminum circuit conductor pattern be formed in the uppermost layer of the multilayer patterns, and the aluminum circuit conductor pattern is visualized due to the fact that the aluminum circuit conductor pattern can be sufficiently brightly sensed in comparison with the lower layers.

On the other hand, the above-described paper entitled "TECHNIQUE FOR MEASURING FINE DIMENSION OF WAFER" shows a method in which, by utilizing the fact that an organic material such as a resist absorbs ultraviolet rays, the ultraviolet rays are used as illumination light. In this case, the resist pattern which is transparent with the visible light is detected as a dark pattern under the ultraviolet rays with a contrast relative to the other parts.

However, in the prior art, in case of the technique disclosed in Japanese Patent Unexamined publication No. 57-208153, if the aluminum conductor layer is included in the lower layers, the aluminum layer of the lower layers is also brightly sensed, so that it would be impossible to distinguish the uppermost pattern from the lower aluminum conductor pattern. Moreover, in this technique, although the bright field illumination and the dark field illumination light are simultaneously projected, in the case where the stepped portions are provided in the insulating layers and the stepped portions of the insulating layer are inclined in such a angle that a regular reflective light from the stepped portions is received by an optical detector system, the regular refractive light from the insulative film stepped portions would be also detected as a light having a relatively large or substantial instensity. In this case, there is a fear that it would be impossible to detect only the conductor pattern.

On the other hand, in the technique disclosed in the paper entiled "TECHNIQUE FOR MEASURING FINE DIMENSION OF WAFER", there is no consideration of the case where the stepped portions are formed in the circuit conductor pattern. In other words, the light projected on the stepped portions of the circuit conductor pattern is reflected sidewards, as a result of which the stepped portions are detected as dark parts and it would be impossible to distinguish the stepped portions from disconnections of circuit conductors.

Accordingly, the first object of the present invention is to provide a method for enhancing a yield of a thin film multilayer substrate which needs a small-amount production system with a high cost.

An additional object of the invention is to provide a method for enhancing an efficiency of the inspection and the repair of the product.

The second object of the invention is to provide a method and an apparatus for detecting a pattern of an upper most conductor pattern layer of a thin film multilayer substrate relative to stepped portions, lower pattern layers, insulating films and the like.

SUMMARY OF THE INVENTION

In order to attain the first object of the invention, there is provided a method for producing a substrate having thin film multilayer circuit conductors in which a plurality of circuit conductor pattern layers are superposed through insulating layers, comprising the steps of: optically detecting the most newly deposited or formed circuit conductor pattern layer whenever the circuit conductor pattern layer is deposited or formed on the substrate; inspecting an absence or a presence of a fault or defect of the circuit conductor layer; and repairing a faulty portion in accordance with fault position data detected by the inspecting. The dielectric layer and conductor pattern layer will be generally deposited further.

According to the present invention, the above-mentioned additional object can be attained by irradiating on exposed surfaces of a conductor pattern layer and dielectric layer(s) with a light beam of a specific range of wavelength where one of an intensity of the reflected light from the dielectric layer(s) and an intensity of the reflected light from the conductor pattern layer is always greater than the other, or by detecting only the light of the specific range of wavelength.

The projecting or illuminating light may be so called white light having frequency or wavelength components greater than and/or less than the specific wavelength region above, if only the light of the specific wavelength region is selectively detected, for example through an appropriate filter. When the illuminating light is irradiated along one direction onto the substrate, the reflected light beams in all directions (ideally over $2\pi$ solid angles), i.e. not only regular reflection but also diffused reflection are detected so as to visualize the uppermost conductor pattern.

When the illuminating light is irradiated in, multi- or omni-directions, the regularly and diffusedly reflected light may be detected in one direction so as to visualize the uppermost conductor pattern.

The fluorescence from the exposed dielectric or insulating layers may be detected selectively so as to detect the uppermost conductor pattern.

According to the method for producing the thin film multilayer substrate, the fault of the most newly formed circuit conductor pattern layer is inspected whenever the circuit conductor pattern is formed, and the faulty portion is repaired. Therefore, there is no fear that the defector faults are accumulated, thus enhancing the yield of the products (i.e., thin film multilayer substrates).

On the other hand, by using a light having the specific wavelength region where one of the intensities of reflected lights from the uppermost conductor pattern layer and from the exposed dielectric layer(s) is always greater than the other, the reflected light from the circuit conductor patterns of the lower layers below the insulating layer is extremely weakened as later described with reference to FIG. 2, whereby it is possible to visualize only the circuit conductor pattern of the uppermost layer. Thus, it is possible not to detect the reflective light from the circuit conductor pattern of the lower layer, defect of which has been already inspected or repaired. Therefore, the efficiency of the inspection and repair is enhanced.

When the pattern having stepped portions is illuminated by a usual bright field illumination in the visualizing and detecting step, the light projected for illumination to the stepped portions of the pattern escapes sidewards as shown in FIG. 3, so that the stepped portions are darkly sensed. In this case, it would be impossible to judge whether these portions are disconnections or stepped portions. However, by detecting the light sidewardly escaping, it is possible to detect the stepped portions as bright portions. Thus, there is no fear that the faulty portions would not be picked up, thereby enhancing the production yield.

In addition, shown in FIG. 4, it is possible to detect the stepped portions by the illumination in an omnidirectional manner.

Furthermore, as explain later in detail with reference to FIG. 26, when an excitation light is irradiated for illumination and the fluorescence from the dielectric layers are detected, the conductor pattern is detected in the form of a dark silhouette on a bright background of the dielectric layers.

According to the present invention, the second object can be attained by an apparatus for detecting a circuit conductor pattern layer of a thin film multilayer substrate, comprising: at least one first illumination light source; a ring light guide having a plurality of ring slant surfaces for emitting an incident light as an illumination light in an oblique circumferential direction relative to the thin film multilayer substrate which is composed by superposing circuit conductor patterns through insulative layers, said slant surfaces being different in slant angle from each other; a bundle of a plurality of optical fibers for introducing the light from said illumination light source to the ring light guide for the illumination from the respective slant surfaces of said ring light guide; a condenser lens for collecting a reflected light component of the illumination light reflected through a central aperture of said ring light guide from said substrate; and a detecting means for detecting a light intensity of the light collected by the condenser lens.

It is preferred that the detection apparatus further comprises a second illumination light source for imparting a vertical incident light onto the substrate through the central aparture of the ring light guide.

According to the present invention, in order to attain the second object, there is also provided a method for detecting a circuit conductor pattern layer, comprising: projecting a linearly polarized light in a wavelength range in which a reflectivity of the circuit conductor pattern layers is higher than that of an insulating layer, onto an exposed surface of the circuit conductor pattern layer and the insulating layers of a sample in which a plurality of thin film multilayer circuit conductors superposed through a plurality of insulating layers and detecting a polarization component, perpendicular to a polarization direction of the illumination light, in the reflected light from the sample.

According to the present invention, in order to attain the second object, there is also provided an apparatus for optically detecting a circuit conductor pattern layer of an uppermost layer of a thin film multilayer circuit conductor substrate in which a plurality of circuit pattern layers are superposed through insulating layers, comprising: a light source for generating a light having a predetermined range of wavelength; an illuminating optical system for obliquely projecting the light from the light source onto the thin film multilayer substrate from a substantially entire circumference; a first polarizer plate disposed between said illuminating optical system and the substrate for polarizing the illumination light from the illuminating optical system, and having an aperture for allowing the reflective light of said illumination light from said substrate; a second polarizer or polarization plate for allowing a light of a polarization component, perpendicular to the polarization direction of the illumination light having passed through the first polarization plate, of reflective light having passing through the aperture to be passed therethrough; and an image detecting means for picking up the reflective light which has passed though the second polarization plate.

According to the circuit conductor pattern detecting method, the linearly polarized light in the wavelength range wherein the reflectivity of the circuit conductor pattern is high is projected to the surfaces of the circuit conductor pattern and the insulating layers, and the polarization component, perpendicular to the polarization direction of the illumination light, of the reflective light from the sample is detected. Therefore, the reflective light from the insulating layer is reduced. Accordingly, it is possible to an improved image of the uppermost circuit conductor pattern.

In addition, according to the circuit conductor pattern detecting apparatus of the present invention, because the light having a predetermined range of wavelength emitted from the light source is projected from substantially all the circumference to the sample, the uppermost circuit conductor pattern is detected with a high contrast. In addition, in the circuit conductor layer detecting apparatus of the present invention, since only the polarization component, perpendicular to the polarization direction of the light having passed through the first polarization plate, of the reflective light from the thin film multilayer substrate is passed through the second polarization plate, the reflective light from the flat portions of the insulating layers is interrupted. Accordingly, it is possible to obtain an improved image of the circuit conductor pattern of the uppermost layer.

BRIEF DESCRIPTION OF THE DRAWINGS

The foregoing and other objects, advantages as well as features of the invention will be made clearer from the description of preferred embodiments with reference to drawings in which:

FIG. 10 is a view showing another embodiment of a pattern visualizing method;

FIG. 11 is a view showing still another embodiment of the pattern visualizing method;

FIG. 19 is a sectional view showing a pattern detecting apparatus according to an embodiment of the invention;

FIGS. 20A and 20B are plan views showing the polarization directions of the polarizer and the analyzer shown in FIG. 19;

DESCRIPTION OF THE PREFERRED EMBODIMENTS

A method for producing a thin film multilayer substrate according to one preferred embodiment of the invention will now be described with reference to FIG. 1.

Figure 1:
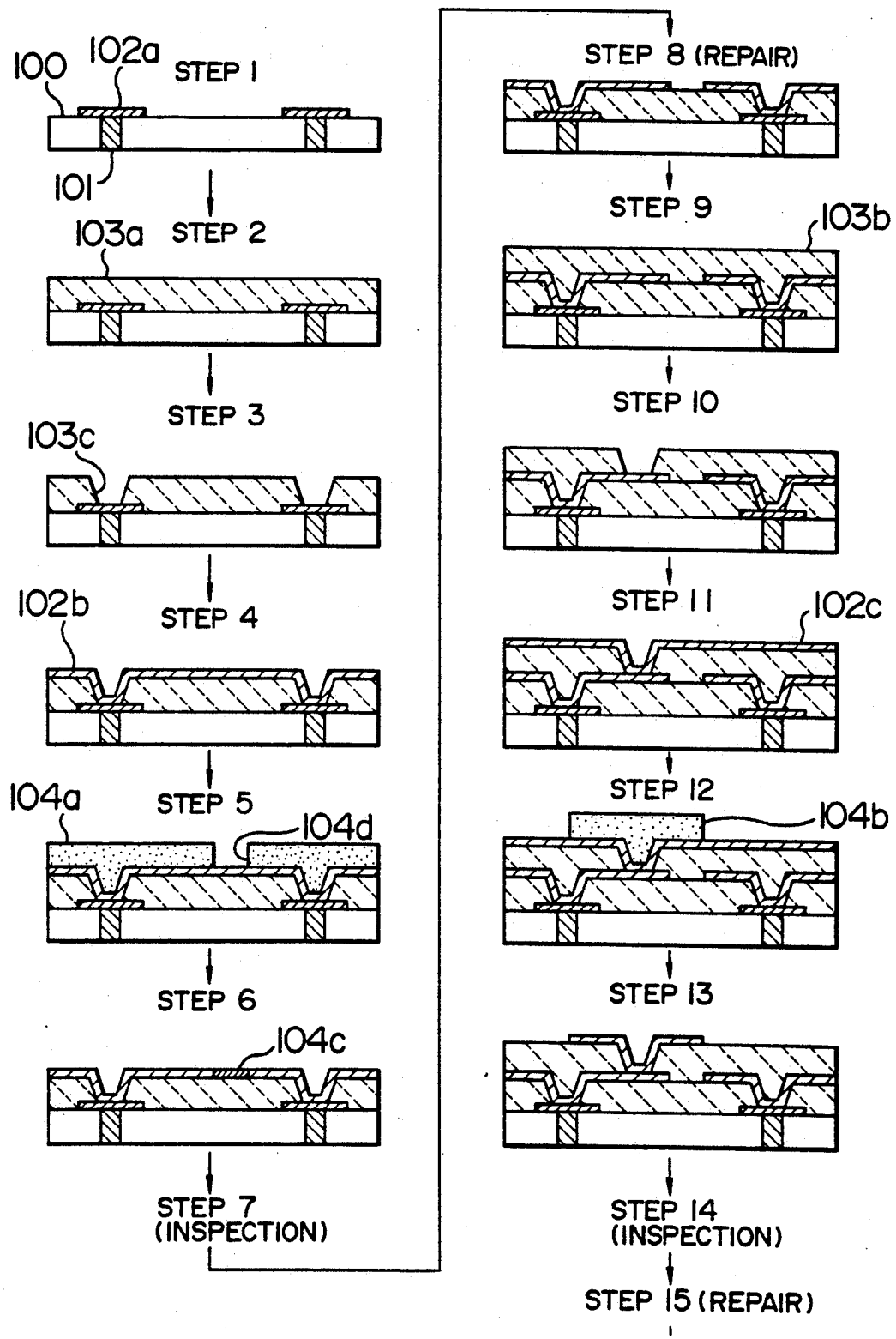
FIG. 1 is a view showing a method for producing a thin film multilayer substrate in accordance with one preferred embodiment of the invention.

In step 1 in FIG. 1, an aluminum circuit conductor pattern 102a is deposited on a ceramic base substrate 100 (having a size of, for example, about 10 cm ×10 cm). In step 2, polyimide type resin layer 103a which is an insulating or dielectric film is deposited, and in step 3, through-holes 103c are formed in the polyimide type resin film 103a. Subsequently, in step 4, an aluminum film 102b is deposited by sputtering. The aluminum deposition may be attained by a vacuum evaporation and any other thin film deposition methods instead of the sputtering. Also, instead of aluminum, an electrically conductive material which forms the circuit conductor pattern may be suitably selected from the conventionally utilized materials for a circuit conductor pattern (or resistance film) such as Au, Cu, Cr, Ni and suitable alloys. A line-width of the circuit conductor pattern is about 20 micrometers at minimum and a pitch between the lines is about 80 μm at minimum. However, these parameters are not limited thereto or thereby, but may be used below or above these minimum levels. In step 5, a photoresist 104a is applied to the aluminum film 102b, and an exposure and a development are carried out in accordance with a mask pattern to form a resist pattern 104a having an opening 104d and the like. In step 6, aluminum is etched, and thereafter the resist 104a is peeled off or removed. Step 6 shows an example in which a short-circuit defect or fault is formed at a position indicated by reference character 104c. In step 7, a pattern inspection is carried out as to the absence or presence of the fault and its position as explained later in detail. In step 8, the fault is repaired in accordance with the inspection result as explained later in detail. After the repair of the fault in step 8, in step 9, an insulating film of polyimide type resin 103b is deposited. In series of steps 10 through 13 corresponding to steps 3 to 6, the circuit conductor pattern 102c is formed Steps 14 and 15 are the repetitive processes of the steps 7 and 8. Thereafter, the steps 9 to 15 are repeated as desired.

In accordance with this embodiment, since, whenever each formation of the circuit conductor pattern has been carried out, the circuit conductor pattern is inspected and the defect(s) or fault(s), if any, is (are) repaired, there is no accumulation of the faults. Namely, there is not any fault remaining except for the uppermost circuit conductor pattern before repairing thereof. Accordingly, it is possible to enhance the yield of the production of the thin film multilayer substrate.

Figure 18:
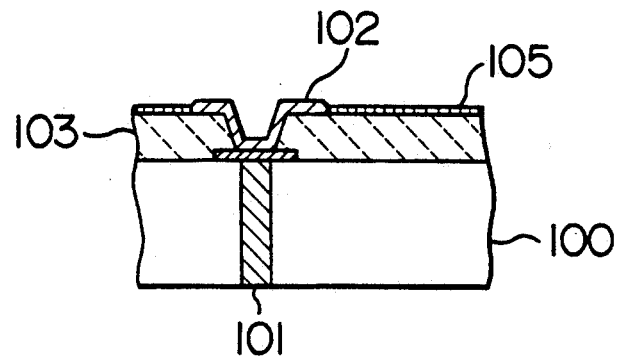
FIG. 18 is a sectional view showing a thin film resistor on the insulating layer.

Although the foregoing embodiment is directed to the method for producing the thin film multilayer substrate composed of insulating films and conductor patterns, it is apparent for those skilled in the art that the invention may be applied to a thin film multilayer substrate in which at least one thin film resistor 105 is formed on the insulating film in addition to the circuit conductor pattern as shown in FIG. 18.

In the foregoing embodiment, it is assumed that the inspection and repair are carried out after the completion of the formation of the circuit conductor pattern. However, at the stage in which a metallic film is deposited on the insulative film, the resist is applied to form the circuit conductor pattern, and then the development process is completed, the inspection and repair may be carried out before removing the resist pattern. In this case, if there would be a fault, the resist pattern is peeled off and a new resist pattern may be again formed for repairing the conductor pattern.

Figure 5:
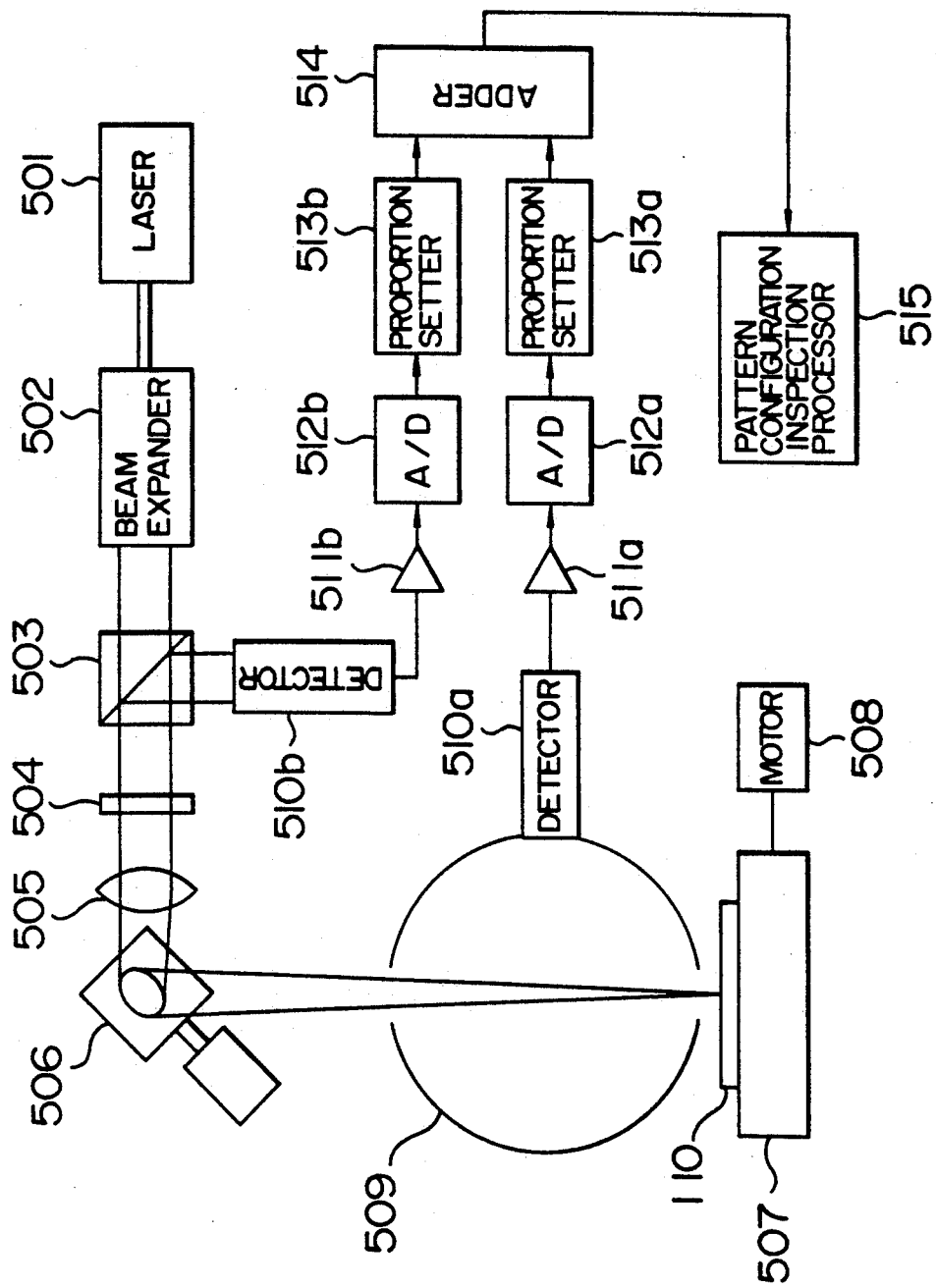
FIG. 5 is a view showing one embodiment of a detecting or visualizing method according to an inspection device used to carry out the method shown in FIG. 1.

FIG. 5 shows an example of a system for carrying out a method of optically detecting or visualizing an uppermost circuit conductor pattern, which is used in the step 7 and the like.

A laser beam emitted from a laser source 501 is linearly polarized and is expanded through a beam expander 502. The beam is caused to pass through a polarization beam splitter 503 which is located so that the linearly polarized component of the laser beam may pass through the beam splitter 503 as remains intact and a ¼ wavelength plate 504 which serves to convert the linear polarization into a circular polarization. The beam is converged to be a spot light having a predetermined size by a condenser lens 505 and is projected to an object 110, i.e., the substrate in the course of production where the processes of steps 6, 13 and the like shown in FIG. 1 have been completed. This spot light is scanned in accordance with the angular position of a scanning mirror 506 provided in the illumination optical path, and a stage 507 is driven in a direction perpendicular to the mirror-scanning direction by a motor 508 to thereby carry out the spot light scanning over the entire surface of the substrate 110 in two directions. Among the reflected lights from the substrate 110, the scattering light reflected sidewards is collected by an integrating sphere 509 and is converted into an electrical signal by a detector 510a having a transducer element and an amplifier 511a. On the other hand, the regular reflection light is caused to pass through the scanning mirror 506 and the condenser lens 505. Then, at the time when the light has passed through the ¼ wavelength plate 504, the circularly polarized beam is converted again into the linearly polarized beam. However, the polarization plane of this linearly polarized beam is perpendicular to the polarization plane of beam emitted from the laser source 501. Thus, the reflective light is now separated from the illumination optical path by the polarization beam splitter 503 and is converted into an electrical signal by a detector 510b having a transducer element and an amplifier 511b. The output signals of the amplifiers 511a and 511b are converted into digital signals by A/D (Analogue-to-Digital) converters 512a and 512b, respectively, and are multiplied by suitable coefficients K1 and K2 by proportion setters 513a and 513b, respectively. Both the resultant signals are added together and sent to a circuit conductor pattern configuration inspection processor 515.

Figure 6:
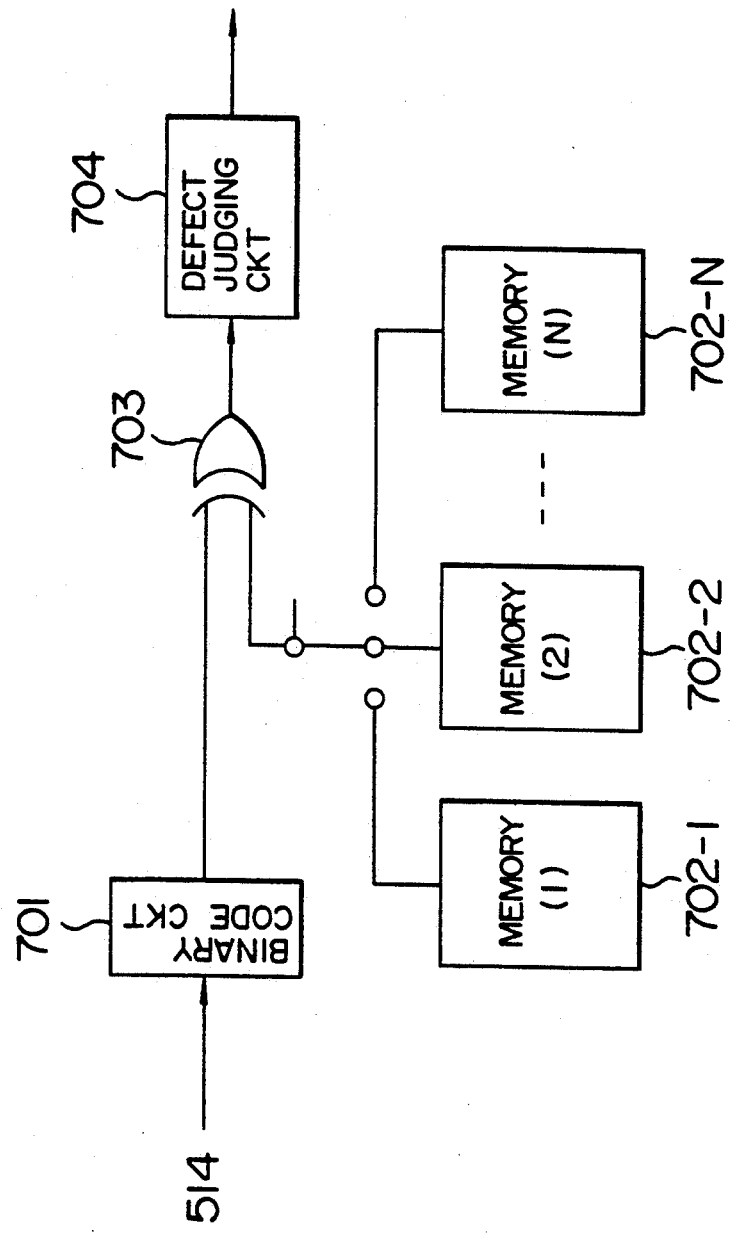
FIG. 6 is a view showing an example of a processing in the detection apparatus used for carrying out the method shown in FIG. 1.

FIG. 6 shows an example of the pattern configuration inspection processor 515 shown in FIG. 5. Normal circuit conductor pattern configurations of respective layers are pre-stored in pattern memories 702-1, 702-2, . . . 702-N. Then, the normal pattern for the uppermost circuit conductor pattern, for example, 702-2 to be now inspected is selected before the inspection. The signal from the adder 514 is converted into binary codes or values by a binary coding circuit 701. In synchronism with the pattern detection, the binary signal representative of the normal pattern of the pattern memory 702-2 is read out. These values are compared in an exclusive OR circuit 703. If there is any difference from the normal pattern, a signal "1" is delivered from the exclusive OR circuit 703, which is detected by a defect or fault judging circuit 704 to deliver a result.

Figure 2:
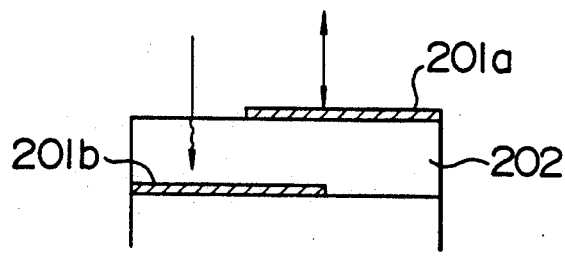
FIGS. 2 to 4 are views showing a reflection of the light at the surface of the thin film multilayer substrate under the manufacture process, respectively.
Figure 3:
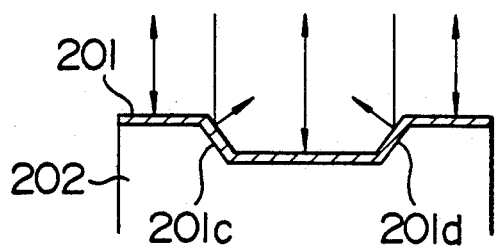
Figure 4:
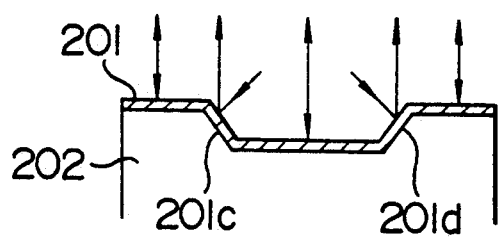
Figure 7:
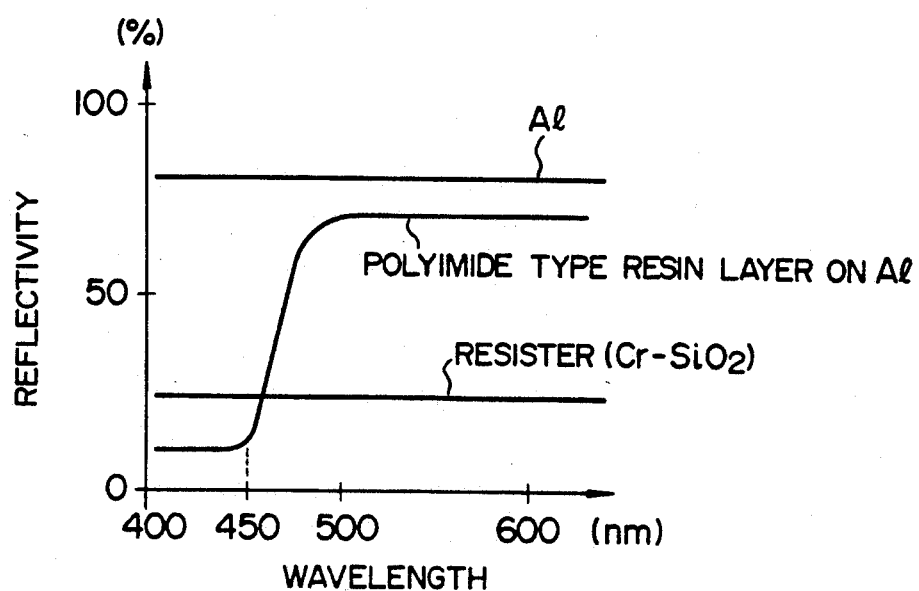
FIG. 7 is a graph showing a dependency, on wavelength, of the reflectivity of the various kinds of material.

The laser source 501 is selected to have a laser beam of a wavelength or wavelengths where a difference or a ratio between reflectivities of the circuit conductor pattern layer and the insulating layer or the resistor layer is large. As shown in FIG. 7, in the case where the circuit conductor pattern is made of aluminum and the insulating film is made of polyimide type resin, the laser beam should have a wavelength of 450 nm or less. This is also the case if a thin film resistor is made of $Cr-SiO_2$. The laser beams which meet these requirements are beams of 442 nm and 325 nm of a He-Cd laser source, beams of 364 nm and 351 nm of an Ar laser source, and the like. As shown in FIG. 2, the spot light projected to the object is reflected upward with a high reflectivity if the circuit conductor pattern 201a is flat. If this reflective light is detected, it is possible to visualize the circuit conductor pattern 201a. However, as shown in FIG. 3, there is a case where the circuit conductor pattern 201 has stepped portions 201c and 210d. The light projected to these parts 201c and 201d are microscopically scattered sidewards. If only the light reflected upwards is detected, the stepped portions 201c and 201d are detected as dark parts, so that it may not be possible to distinguish these parts 201c and 201d from the insulating film portion 202. Accordingly, in addition to the regular reflection light, the so-called scattered light is collected by the integrating sphere 509 for detection to be added to the output from the detection signal due to the regular reflection light, whereby it is possible to visualize the pattern, i.e., to detect the presence of the conductor pattern even if the conductor pattern has the stepped portions. There is also a case due to the condition of formation of the circuit conductor pattern where the regular reflection component of the reflective light is small and the scattered light component thereof is large. In this base, it is possible to visualize the circuit conductive pattern only with the detection of the scattered lights. These cases will be explained in detail later.

In the foregoing embodiment, after the conversion into the digital signals, the regular reflection light detection signal and the scattered or difusedly reflected light detection signal are multiplied by the coefficients K1 and K2 respectively for compensating for the difference in detection sensitivity of the detectors 510a and 510b and the detection efficiencies of these outputs in the proportion setters 513a and 513b, respectively. It is thus possible to readily change the coefficients K1 and K2 in accordance with the instruction from the computer or the like.

Although, in this embodiment, the spot light is scanned by the rotation displacement of the scanning mirror 506, it is a matter of course that the spot light scanning may be attained by a rotary polyhedron or an acoustoptic element.

Figure 8:
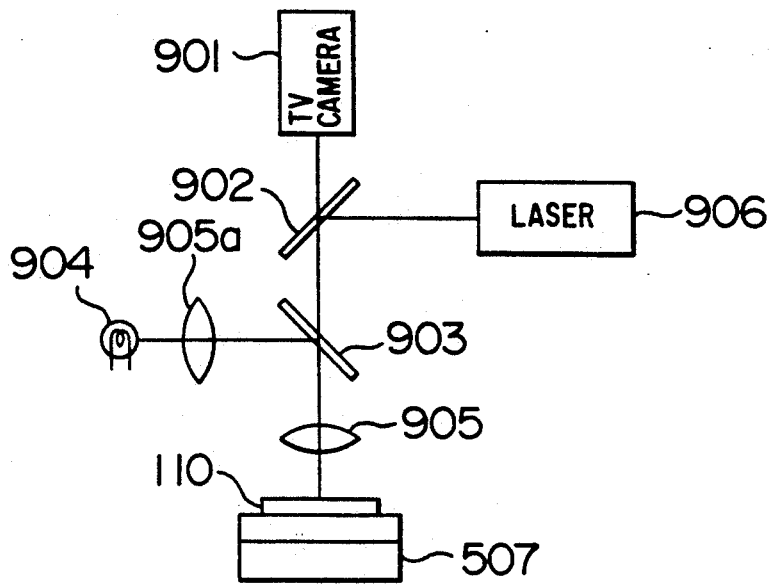
FIG. 8 is a view showing a first embodiment of a pattern repairing apparatus used for carrying out the method shown in FIG. 1.
Figure 9:
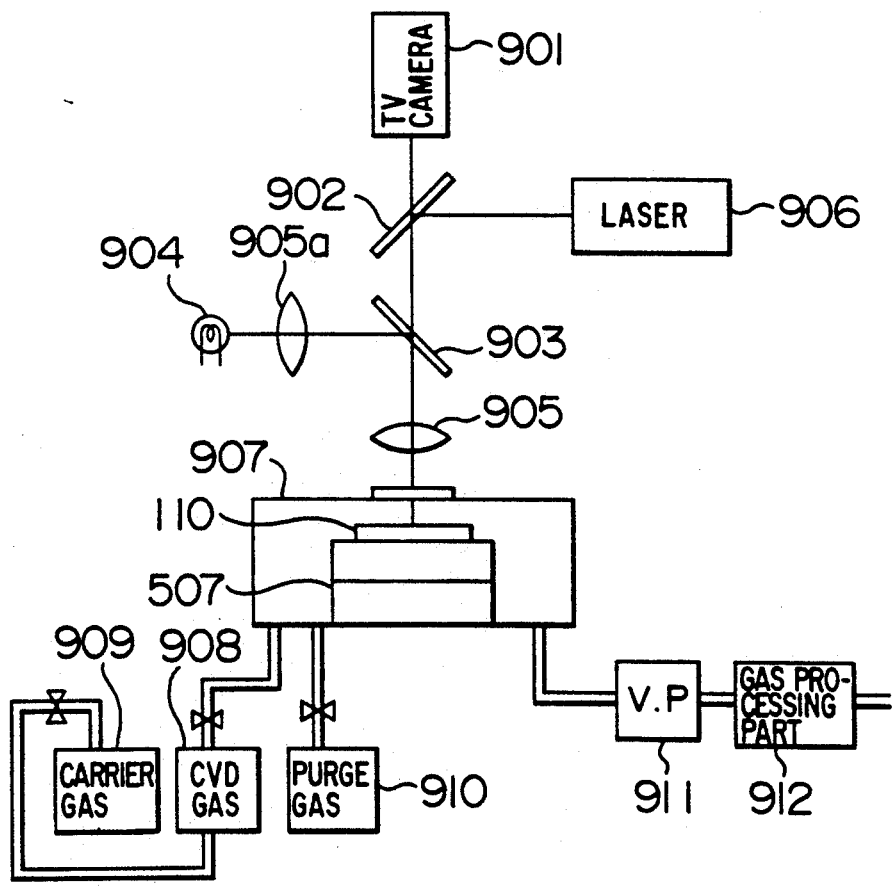
FIG. 9 is a view showing a second embodiment of a pattern repairing apparatus used for carrying out the method shown in FIG. 1.

FIGS. 8 and 9 show examples of the circuit conductor pattern repairing device to be used in the steps 8, 15 and the like shown in FIG. 1.

FIG. 8 shows a device for cutting or trimming an excess or extra part of the circuit conductor pattern by the laser beam in the case where the extra part remains in the circuit conductive pattern layer after the steps 6, 13 or the like. In the repairing device, an x-y stage 507 is moved in a plane perpendicular to the irradiated laser beam on the basis of the positional data of a defect or fault given by the inspection device as shown in FIG. 5. Then, the substrate 110 which is a sample in the midway of the manufacture process is illuminated by a light source 904 through a lens 905a, a half-mirror 903 and a lens 905. The fault is confirmed by a TV camera 901 as to whether the portion inspected to be a defect or fault is actually the defect or fault to be repaired or not. If this should be repaired, the fault is repaired by projection of the laser beam from a laser device 906 through a half-mirror 902, the half mirror 903 and the lens 905.

FIG. 9 shows a device for splicing or depositing an additional circuit conductor, in the steps 8, 15 and the like of FIG. 1, to a disconnected defect or fault part of a circuit conductor pattern is partially disconnected after the steps 6, 13 and the like shown in FIG. 1. An x-y stage 507 is moved on the basis of the positional data of the defect or fault, and the fault to be repaired is confirmed by using a light source 904 and a TV camera 901. Then, CVD gas 908 is introduced into a chamber 907, and a reaction is generated at the portion and/or in the vicinity of the fault by a laser beam from a laser source 906 to thereby splice or add a circuit conductor to the portion to be repaired (i.e., the faulty portion). The CVD gas is selected in conformity with the material of the conductor pattern layer. For example, for the aluminum pattern, the gas may be tri-methyl aluminum or tri-isobutyl aluminum. The laser source 906 may be selected from an excimer laser, an Ar laser, a YAG laser and the like. In FIG. 9, reference numeral 909 denotes a carrier gas receiving tank, reference numeral 910 denotes a tank for receiving purging gas, numeral 911 denotes a vacuum pump, and numeral 912 denotes a exhaust gas processing unit.

A second embodiment of a system for visualizing an uppermost layer pattern is shown in FIG. 10. A regular reflection light is picked up by a half-mirror 521 and a condenser lens 522 instead of the polarization beam splitter 503 and the ¼ wavelength plate 504 in the embodiment of FIG. 5. Similarly to the case in FIG. 5, the regular reflection light detection signal and the scattered light detection signal are added together by an operational amplifier 520. According to this embodiment, it is possible to pick up the signals of the regular reflection light and the scattered light with a simple structure.

FIG. 11 shows a third embodiment of a system for visualizing an uppermost layer pattern. According to the third embodiment, a bright field illumination and a dark field illumination are performed simultaneously, and a light having a specific range of wavelengths is allowed to as through a filter 607 for detection. The bright field illumination is adapted to project the light from a light source 601b onto a sample 110, i.e., the substrate under the manufacture process, through a half-mirror 604 and an objective lens 605. On the other hand, the dark field illumination is adapted to project the light from a light source 601a onto the sample 110 with the light beam being made parallel beam by a parabolic mirror 602. Although the pattern image is focused on a detector 608 by the objective lens 605, it is to be noted that the filter 607 is disposed prior to the detector 608 to allow the light having the specific range of wavelengths to pass through the filter 607. A mercury lamp or a xenon lamp may be used as the light source 601a or 601b. A parabolic mirror or a polyhedral mirror may be used as the dark field illumination mirror 603. According to this embodiment, since an image of the circuit conductor pattern is formed by the objective lens 605, it is possible to use an image pickup device such as linear sensor or an area sensor as the detector 608 to thereby readily pick up the detection image.

Figure 12:
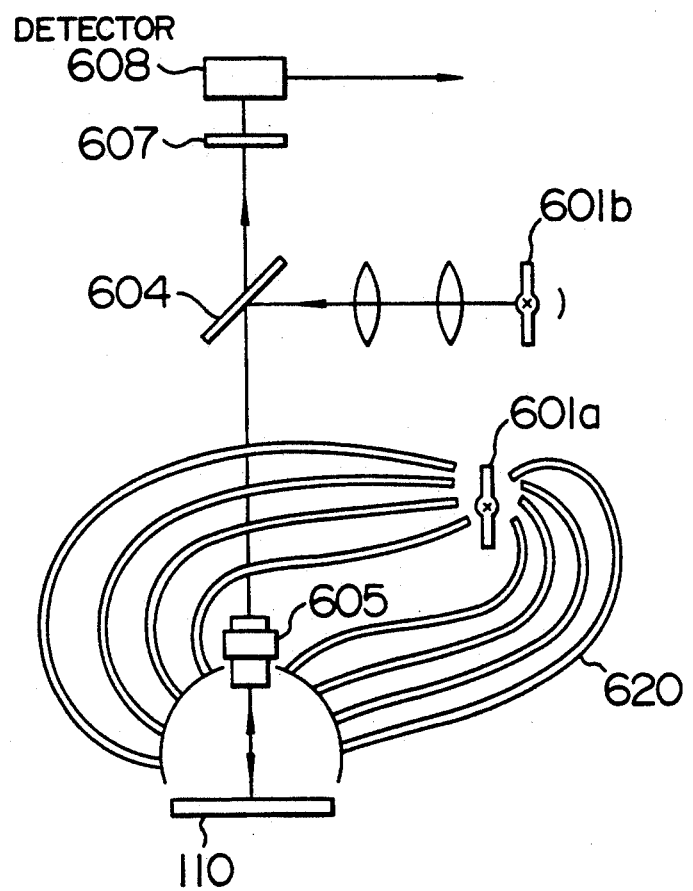
FIG. 12 is a view showing still another embodiment of the pattern visualizing method.

FIG. 12 shows a fourth embodiment of a method for visualizing the uppermost conductor layer pattern. According to this embodiment, the light of mercury lamp 601a is caused to propagate through a plurality of optical fibers or fiber bundles 620 and to project the light on the sample 110, i.e., the substrate under the manufacture process in an omnidirectional manner. At the same time, the light from a mercury lamp 601b is projected on the substrate 110 by a half-mirror 604. The reflective light from the substrate 110 is received by an objective lens 605 and a light having wavelengths of 450 nm or less is caused to pass through a filter 607 to thereby detect the image of the uppermost conductor pattern by a detector 608. According to this embodiment, the exit ends of the optical fibers 620 are located uniformly on a semispherical surface around the substrate 110 but it is also possible to arrange them as shown in FIG. 13 so that the ends of the optical fibers 620 are confronted uniformly with a first ring surface 631 of an annular light guide 630 as well as a second ring surface 632 thereof.

Figure 13:
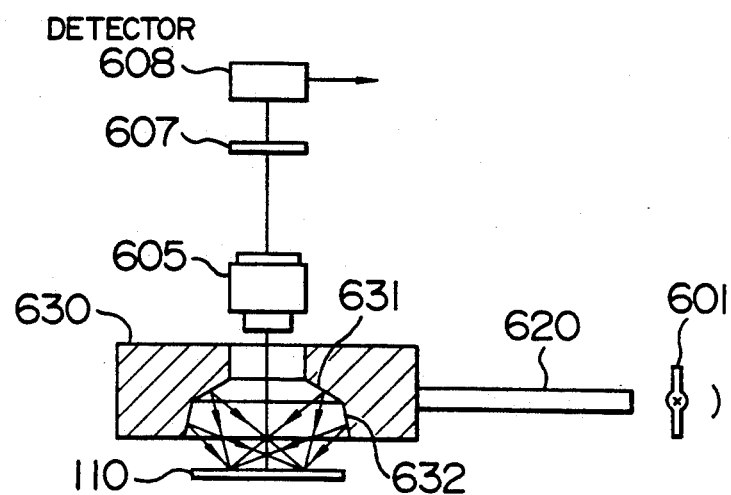
FIG. 13 is a view showing still another embodiment of the pattern visualizing method.

More specifically, in the case where a surface roughness of the circuit conductor pattern surface is relatively large, as shown in FIG. 13, because the illumination light is diffusedly reflected at the conductor pattern surface the illumination may be only the dark field illumination such as the illumination at the restricted angles as defined by the two ring light guide portions 631 and 632 to detect the circuit conductor pattern distinguishing it from the insulating film.

Figure 14:
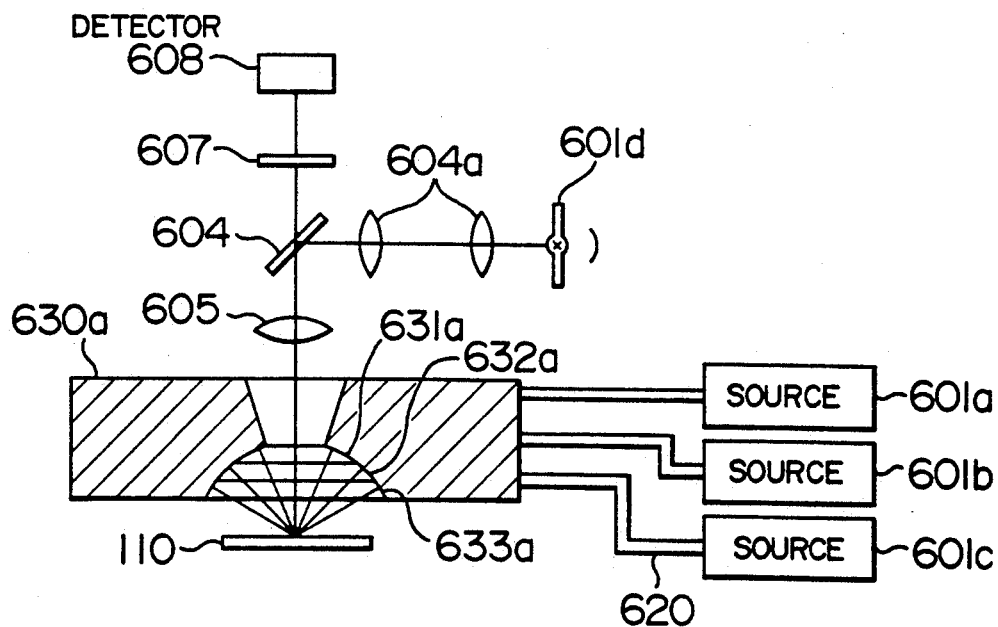
FIG. 14 is an illustration of a modification of FIG. 13.
Figure 15:
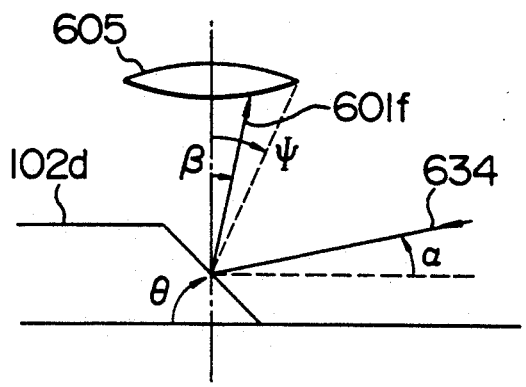
FIG. 15 is an illustration showing a relationship between the regular reflection at the slant stepped portions of the circuit conductor pattern and an aperture diameter of the objective.
Figure 16:
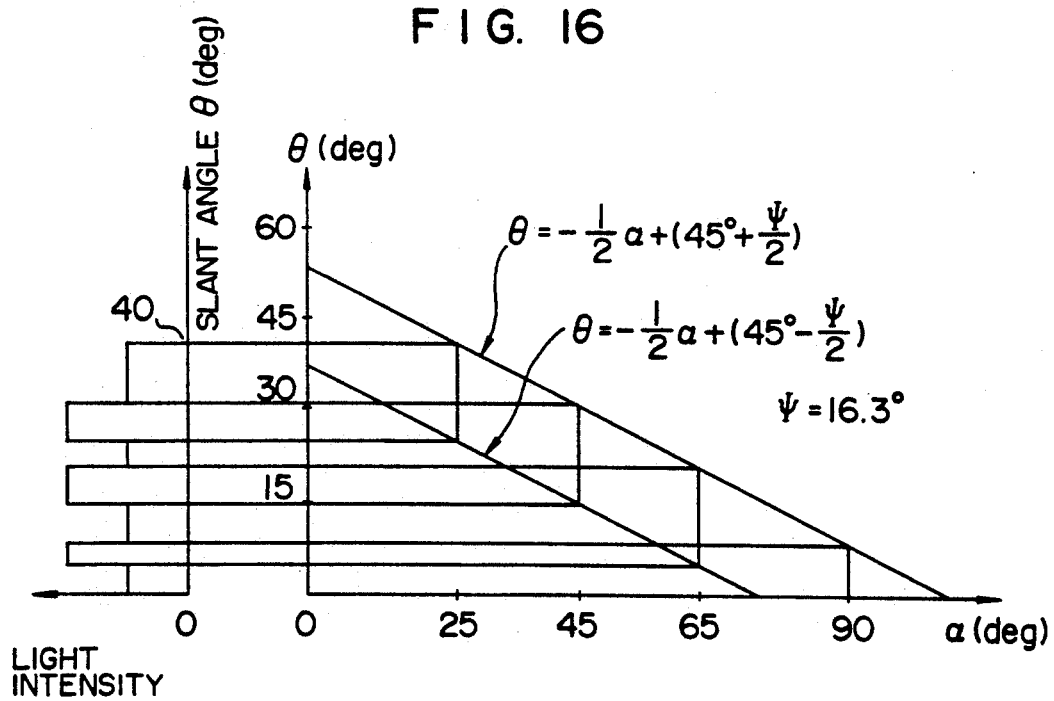
FIG. 16 is a graph showing a relationship between the stepped portion slant angle $\theta$ and the light intensity of the light received by the objective in the case where the illumination light is given at four specific angles.

On the other hand, in order that the image is detected at the restricted illumination angle irrespective of the surface roughness of the circuit conductor pattern surface, as shown in FIG. 14, a bright field illumination system composed of a light source 601d, a lens 604a and a half-mirror 604 is added in cooperation with a lens 605 to the apparatus shown in FIG. 13. In FIG. 14, dark field illumination is applied through the optical fibers or fiber bundles 620 through three annular end faces 631a, 632a and 633a from three optical sources 601a, 601b and 601c, respectively. In the case where the surface roughness of the surface of the circuit conductor pattern is relatively large, since the illumination light is diffusedly reflected at the surface of the circuit conductor pattern of the substrate 110, it is easy to detect the circuit conductor pattern. However, in the case where the surface roughness of the circuit conductor pattern is small, since the illumination light is almost regularly reflected, it is necessary to receive the reflective light by the objective lens 605. More specifically, in the case where the surface roughness is small, as shown in FIG. 15, if the following relationship is met, it is possible to receive the regular reflection light by the objective lens 605:

$$90° - \Psi \leq 2\theta + \alpha \leq 90° + \Psi$$

where $\theta$ is a slant angle of the circuit conductor pattern 102d at the stepped portion, $\alpha$ is an illumination angle of the illumination light 634 and $\Psi$ is an aperture angle of the objective lens 605. For example, in the case where the bright field illumination $\Psi = 90°$ and the three-stages of dark field illumination $\alpha = 25°$ C., 45 and 65, and the numerical aperture NA of the objective lens 605 is at 0.28 (aperture angle $\Psi = \sin^{-1}(NA)$), it is possible to detect the circuit conductor pattern 102d having the inclination of $0° \leq \theta \leq 40°$, as shown in FIG. 16, where substantial intensity of light is received by the lens 605.

According to this embodiment, since it is easy to illuminate the substrate from the multiple directions it is possible to suppress nonuniformity in illumination on the substrate 110 and it is easy to detect the pattern having the stepped portions.

Figure 17:
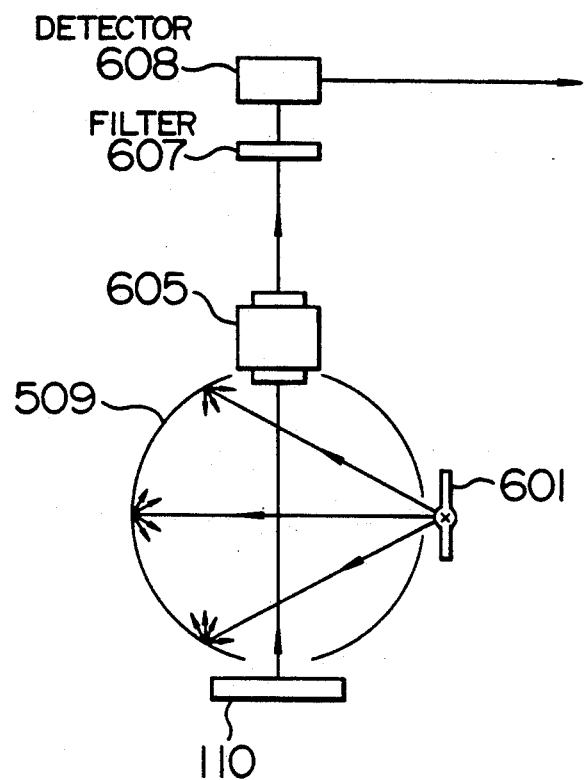
FIG. 17 is a view showing still another embodiment of the method for visualizing the pattern.

FIG. 17 shows a fifth embodiment of a method for visualizing the uppermost layer pattern. According to this embodiment, the light source 601 is arranged relative to the integrating sphere 509 so that the light from the light source 601 is not directly applied to the substrate 110 under the manufacture process. Since the inner wall of the integrating sphere 509 is coated with a substance such as barium sulfate which causes the inner wall to be a perfectly diffused reflection surface with a high reflectivity, the light is projected to the substrate 110 from the overall inner circumferential surface of the sphere 509. The reflective light from the substrate 110 is received by the detecter 608 through the objective lens 605 and the filter 607 to be delivered in the form of an electric signal indicating the image of the conductor pattern.

According to this embodiment, since the substrate 11 is projected in the omunidirectional manner, it is possible to obtain a substantially uniform illumination, and it is very easy to detect the circuit conductor pattern having the stepped portions.

As described above, according to the present invention, since the circuit conductor pattern of the uppermost layer is visualized and inspected in the manufacturing process of the thin film multilayer substrate, and after the repair of the fault, the subsequent layer is deposited thereon, the patterns of the lower layers which have been already repaired and inspected are not detected, thus enhancing the efficiency of the repair.

The above-mentioned embodiments of FIGS. 11, 12, 13, 14 and 17 where illumination is given onto the substrate surface from various or multiple directions, and where light of a limited range of wavelength(s) reflected from the substrate in a direction is detected to detect or visualize the uppermost conduction pattern layer, can be improved by utilizing polarizer-analyzer system, in the case where the surface roughness of the conductor pattern layer is much higher than that of the insulator or dielectric layer as explained in detail hereinafter referring to FIGS. 19 to 25.

FIG. 19 is a sectional view showing still another pattern detection or inspection device according to the invention.

In FIG. 19, a light source 301 is provided for projecting a light onto a sample, i.e., a thin film multilayer substrate 300 under the manufacture process (for example, step 7 and 14 in FIG. 1), and a bundle of fibers 302 is arranged to guide the light from the source 301.

At a terminal end of the fiber bundle 302, there is provided a ring light guide 303 for illuminate the light from the light source 301 onto the thin film multilayer substrate 300. The light guide 303 is located above the thin film multilayer substrate 303. An objective lens 304 is arranged through an analyzer element 308 above the annular light guide 303. A detector 306 is located at a focal point or image-forming point of the objective lens 304. A filter 305 is interposed between the light source 301 and the fiber bundle 302. A polarizer 307 is arranged below the light guide 303.

The light guide 303 is formed so that the exit end faces of the optical fibers 302 are disposed in the form of a circle, and the light is obliquely projected from all the circumference. Only the light having a range of wavelengths such that the reflectivity of the circuit conductor layer is high and the transmittance of the insulating layers is low is caused to pass through the filter 305. The polarizer 307 is disposed in the oblique illumination path for converting the light from the light guide 303 into a linearly polarized light. The analyzer element 308 is arranged so that its polarization direction is perpendicular to the polarization direction of the polarizer 307 as shown in FIG. 20A which shows plan views of the analyzer element 308 and the polarizer 307, respectively. An aperture 307a is formed in the central portion of the polarizer 307 so that the reflective light passing through the aperture 307a is transferred on the detection side without any additional change of polarization.

Figure 21:
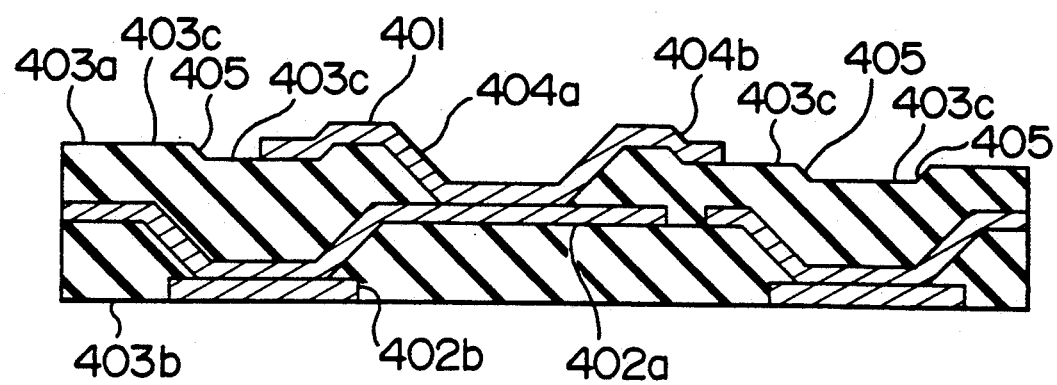
FIG. 21 is a sectional view showing a detail of the structure of the thin film multilayer substrate.

In FIG. 21 showing the thin film multilayer substrate 300, the uppermost layer is a circuit conductor pattern layer 401 made of aluminum, and lower circuit conductor patterns 402a and 402b made of aluminum are arranged below the uppermost layer 401 in this order. Insulating films or layers 403a and 403b made of polyimide type organic material are respectively interposed between the adjacent conductor pattern layers. The uppermost circuit conductor pattern layer 401 has stepped portions 404a and 404b, and the insulating film 403a has also stepped portions 405.

As described before, in order to produce a large amount of thin film multilayer substrates with a high yield, it is desired to adopt a manufacture method such that, whenever each conductor layer is formed, the uppermost circuit conductor layer is inspected to check presence/absence of a fatal fault or defect of the circuit conductor pattern, and after the repair of the faulty portion, the subsequent layer is formed. In this case, since the lower circuit conductor pattern is always subjected to the inspection and repair, the layer to be inspected is only the uppermost circuit conductor pattern layer at that time. The uppermost layer pattern is sensed while distinguishing from the insulating layers and the lower circuit conductor pattern layers and is visualized, thereby enhancing the efficiency of the inspection.

The detection operation of the apparatus or the detecting or visualizing method according to still another embodiment of the invention will be explained with reference to FIGS. 20A and 21 as well as FIG. 19.

The light emitted from the light source 301 is projected onto the thin film multilayer substrate 300, having subjected to, for example, the steps 1 through 13 shown in FIG. 1, through the filter 305, the fiber bundle 302, the light guide 303 and the polarizer 307. The reflective light from the thin film multilayer substrate 300 reaches the detector 306 through the analyzer element 308 and the objective lens 304 for detection.

In order to more readily understand this embodiment of the invention, a preferred pattern detecting method will be explained prior to the details of the embodiment.

Figure 22:
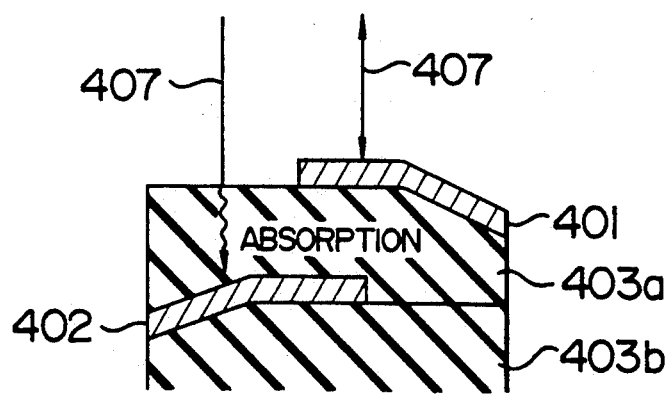
FIG. 22 is a view showing an absorption of the illumination light by the insulating film.
Figure 21:
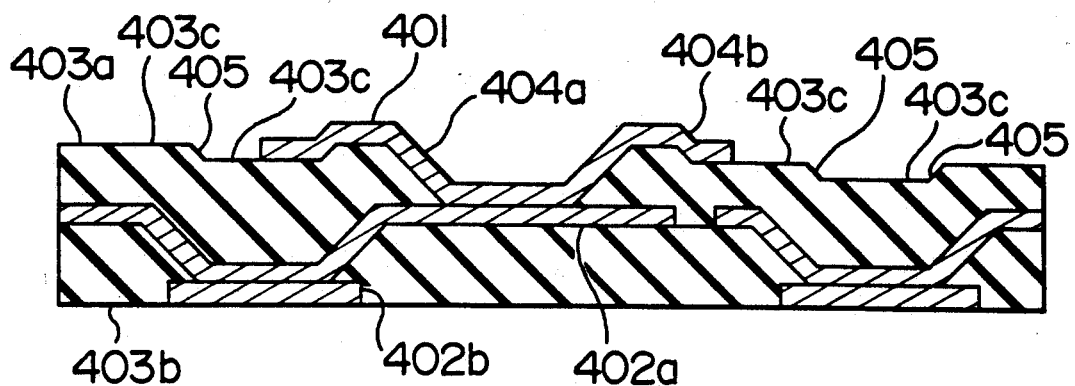
Figure 22:
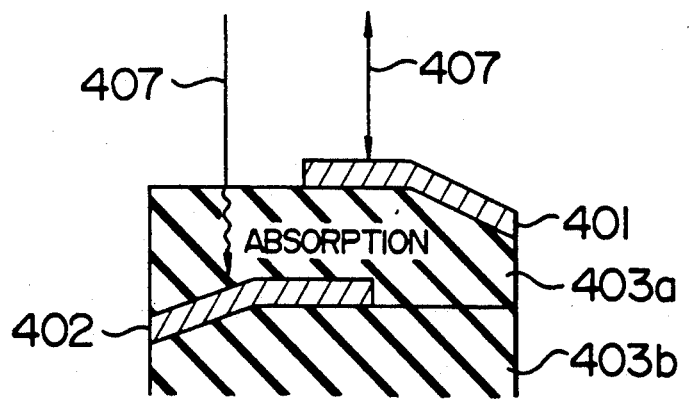

First of all, the explanation will be made as to the case where a range of wavelengths of the illumination light is limited such that the intensity of light reflected by the insulating layers is lower than that reflected by the uppermost circuit conductor pattern layer. The insulating films or layers of the thin film multilayer substrate made of resin(s) are generally transparent or semitransparent relative to a visible light and are small in thickness. Accordingly, in the case where a normal white light is used as the illumination light, the uppermost conductor pattern layer and the lower conductor pattern layer(s) are detected with the same brightness, so that it may not be possible to distinguish the patterns. Therefore, by using as the illumination light the light having a range of wavelength(s) such that the transmittance of the insulating film is small and the reflectivity for the circuit conductor pattern is high, as shown in FIG. 22, the intensity of the reflective light from the lower circuit conductor pattern layer 402 located below the insulating film or layer 403a is extremely lowered, thus enabling the distinction between the circuit conductor pattern 401 of the uppermost layer and the circuit conductor pattern 402 of the lower layer. In this case, the "low transmittance" means such a level of transmittance that the intensity of the reflective light from the circuit conductor pattern 402 of the lower layer through the insulating layer 403a having a thickness of about 5-10 micrometers is negligibly lower than the intensity of the reflective light from the circuit conductor pattern 407 of the uppermost layer.

Figure 23:
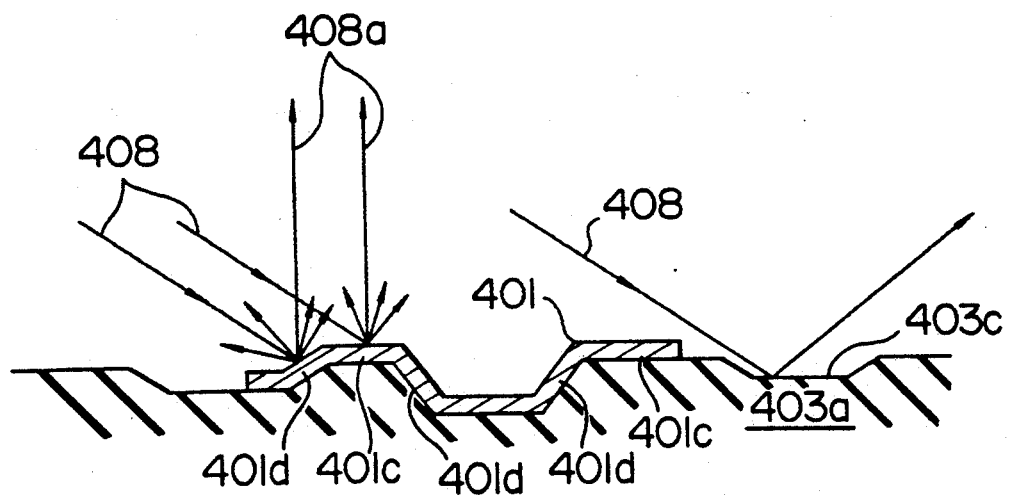
FIGS. 23 and 24 are views showing the reflection at the stepped portions of the circuit conductor pattern of the uppermost layer.

Subsequently, the case where the illumination is performed obliquely from the overall circumference of the thin film multilayer substrate 300 will be explained. In the case where the aluminum layers or the like are formed by sputtering or the like, the surface of the circuit conductor pattern layer is generally rough, whereas the surface of the insulating film or layer made of polyimide resin or the like is generally smoother than that of the conductor pattern layer. Accordingly, as shown in FIG. 23, if the illumination 408 is projected obliquely onto the thin film multilayer substrate and a reflective light 408a reflected vertically relative to the thin film multilayer substrate is to be detected, due to the fact that the surface of the circuit conductor pattern 401 is rough, a diffused reflection occurs. As a result, it is possible to brightly detect both the flat portions 401c and the stepped or slant portions 401d. In contrast thereto, since the surface of the insulating film 403a is smooth, almost no diffused reflection occurs, and the light reflected from the flat portions 403c of the insulating film 403a escapes sidewards so that the reflective light therefrom is not detected. Namely, the oblique illumination makes it possible to detect the circuit conductor pattern of the uppermost layer with a high contrast. Thus, when the overall circumferential oblique illumination is applied to the substrate, a conductor pattern layer having any configuration irrespective of the slant directions and angles of the slanted surfaces of the stepped portions can be visualized, so long as the conductor pattern layer has rougher surface than the insulating resin layer.

Figure 24:
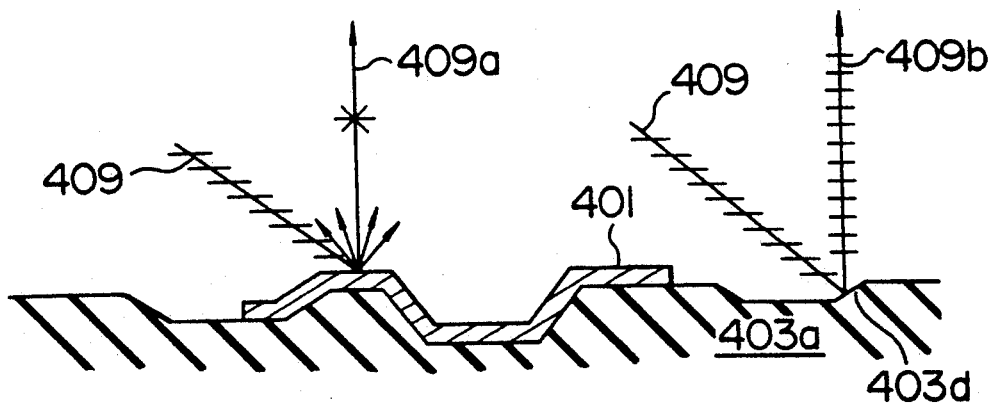

Now, the case where the illumination light is the linearly polarized is explained further. As described above, in the case where the vertically reflected light is detected under the oblique illumination, there is no fear that the reflective light from the flat portions 403c of the insulator film or layer would be detected. However, if there is a stepped portion, in the insulator film, having a slant angle such that the light is regularly reflected upwardly, the regular reflection light from tis stepped portion would be detected. Thus detected light intensity may become the same as or more than the intensity of the reflective light from the uppermost circuit conductor pattern layer. Accordingly, in order to more exactly detect the uppermost circuit conductor pattern layer, it is preferred to remove the regular reflection light from the stepped portions of the insulating film. For this reason, the polarization of the light is utilized. As shown in FIG. 24, when an oblique illumination 409 of linearly polarized light is projected to the thin film multilayer substrate, the reflective light 409a from the circuit conductor pattern layer 401 becomes random-polarized due to the surface roughness of the pattern 401. In contrast, the reflective light 409b from the insulating film 403a is kept linearly polarized in the same polarization direction as that of the incident oblique illumination. Accordingly, if a polarization component, of reflected light, perpendicular to the polarization direction of the incident oblique illumination light is detected, it is possible to remove the vertical regular reflection light 409b from the stepped portions 403d of the exposed insulating layer.

The foregoing three kinds of methods are used in combination, whereby it is possible to more brightly detect the circuit conductor pattern of the uppermost layer of the thin film multilayer substrate without fail than the lower patterns and insulating films which constitute the background.

Turning back to FIG. 19, the operation of the pattern detecting or visualizing device according to an embodiment of the invention will now be described.

When the linearly polarized light having a specific range of wavelength(s) is obliquely projected onto the thin film multilayer substrate 300, the flat portions and the stepped portions 404a and 404b of the circuit conductor pattern 401 of the uppermost layer shown in FIG. 21 causes the random-polarized and diffusedly reflected light. On the other hand, the flat portions 403c and the stepped portions 405 of the insulating film 403a causes the linearly polarized light by regular reflection.

In the reflective light, the light reflected from the flat portions 403c of the insulating layer 403a escapes sidewards, and the light reflected from the stepped portions 404a and 404b of the circuit conductor pattern 401 of the uppermost layer and the stepped portions 405 of the insulating layer 403a is introduced into the analyzer element 308. When the reflective light is received by the analyzer element 308, since the analyzer element 308 is arranged so that the polarization direction thereof is perpendicular to that of the linearly polarized light reflected from the insulating film 403a, the reflective light of the insulating film 403a is prevented to pass by the analyzer 308. In contrast, since the reflective light of the circuit conductor pattern layer 401 is random-polarized and has various polarization components, only a part of the polarization component is prevented to pass through the analyzer 308. In addition, since the wavelength range is restricted by the filter 305, the intensity of the reflective light from the pattern of the lower layers below the insulating layer 403a is extremely lowered to be negligible in comparison with the intensity of light from the bright circuit conductor pattern 401 of the uppermost layer. According to the structure shown in FIG. 19, it is therefore possible to obtain a detection image such that only the uppermost circuit conductor pattern layer 401 is bright and it is easy to distinguish the region corresponding to the uppermost circuit conductor pattern layer 401 from the other region.

The multilayer substrate was subjected to the steps 1 through 6 or 13 in accordance with the manufacture process shown in FIG. 1 and in which the circuit conductor pattern layer(s) was(were) formed by the aluminum sputtering under the normal or conventional condition and the insulating layer was made by application of polyimide type resin. In the case where unpolarized beam illumination or detection of light without polarization is performed, a measured ratio in the intensity of regular reflection light from the stepped portions of the circuit conductor pattern 401 with respect to that from the insulating film 403a in the thus formed substrate was about 1.2, whereas in the case of the polarized beam illumination and the polarized beam detection as explained hereinbefore, the ratio was about 6.4. Namely, a signal-to-noise ratio therebetween was enhanced about five times.

Instead of providing separately the polarizer 307 and the analyzer element 308, it is possible to arrange these elements integrally with each other as shown in FIG. 20B at the position of the polarizer 307. The light source 301 may be a mercury lamp, a xenon lamp, a halogen lamp and the like. It is possible to use a TV camera, a linear image sensor or the like as the detector 306. Furthermore, it is possible to interpose the filter 305 between the objective lens 304 and the detector 306.

Figure 25:
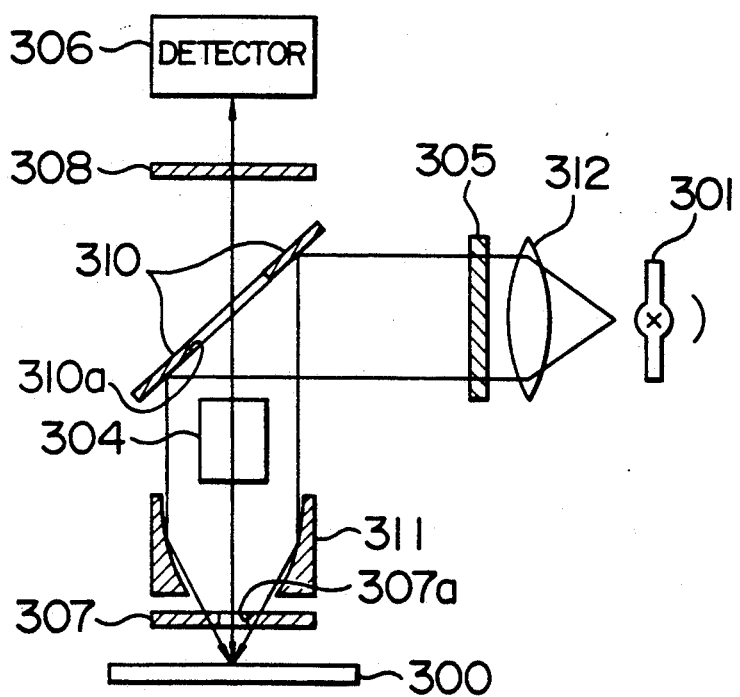
FIG. 25 is a sectional view showing still another embodiment of the pattern detecting apparatus of the invention.

FIG. 25 is a sectional view showing a detecting or visualizing method according to still another embodiment of the invention. In FIG. 25, the same reference numerals are used to indicate the like components or members as those in FIG. 19. The explanation therefor is omitted hereunder.

In this embodiment, a mirror 310 having an opening 310a and a dark field mirror 311 having a parabolic surface of revolution are used instead of the light guide 303, and an objective lens 304 is interposed between the mirror 310 and the dark field mirror 311. In addition, the optical fiber bundle 302 is dispensed with, and instead thereof, a lens 312 for collimation is interposed between a light source 301 and a filter 305. In this case, the combination of the polarization directions of the polarizer 307 and the analyzer 308 is the same as that shown in FIG. 20A.

According to this system, after the light emitted from the light source 301 has been collimated through the lens 312, a light, having a predetermined range of wavelength(s), of the beams from the light source 301 is allowed to pass through the filter 305. Subsequently, the light is deflected in the perpendicular direction by the mirrors 310 and is deflected and irradiated toward the thin film multilayer substrate obliquely from the entire circumference by means of the dark field mirror 311. Then, the linearly polarized light is projected through the polarizer 307 onto the thin film multilayer substrate 300. The reflective light of the thin film multilayer substrate 300 passes through an aperture 307a of the polarizer 307 and reaches the analyzer 308 through the objective 304. The analyzer 308 serves to prevent the reflective light of the insulating film 303a from passing therethrough and allows only a part of the reflective light of the uppermost circuit conductor pattern layer 401 to pass therethrough to be introduced into the detector 306.

According to this embodiment, since there is no transmission loss due to the optical fibers, it is possible to reduce the loss of light emitted from the light source 301. In addition, since the illumination light is collected by the dark field mirror, and hence intensity of the illumination per unit of the sample or object may be considerably increased, to thereby enable the high speed detection.

The embodiments of the present invention concerned with FIGS. 19 to 25 may enjoy the following advantages with the above-described structures.

Namely, in the case where the linearly polarized light of a wavelength range in which a reflectivity of the circuit conductor pattern is high is projected to the exposed surfaces of the conductor pattern and the insulating film of the sample (substrate) to which the thin film multilayer conductor pattern(s) is(are) applied, and the polarization components perpendicular to the polarization direction of the illumination light are detected from the reflective light from the sample, only the circuit conductor pattern of the uppermost layer of the thin film multilayer substrate can be detected or visualized more brightly without fail, and the high quality image of the circuit conductor pattern of the uppermost layer can be obtained for the inspection.

In case of generating the light having a predetermined range of wavelength(s) from the light source, projecting the light from the light source portion onto the thin film multilayer circuit conductor substrate obliquely from the entire circumference by the optical illumination system, linearly polarizing the light by the first polarizer plate having an aperture, allowing the reflective light from the substrate to pass through the aperture of the polarizer plate, allowing only the polarization component, of the reflected light, perpendicular to the polarization component of the illuminating light from the first polarizer plate to pass through a second polarization plate, and picking up the reflective light which has passed through the second polarizer by the detector, it is possible to detect only the polarization component perpendicular to the polarization component of the illumination light, thereby obtain the excellent image of the circuit conductor pattern of the uppermost layer.

Figure 26:
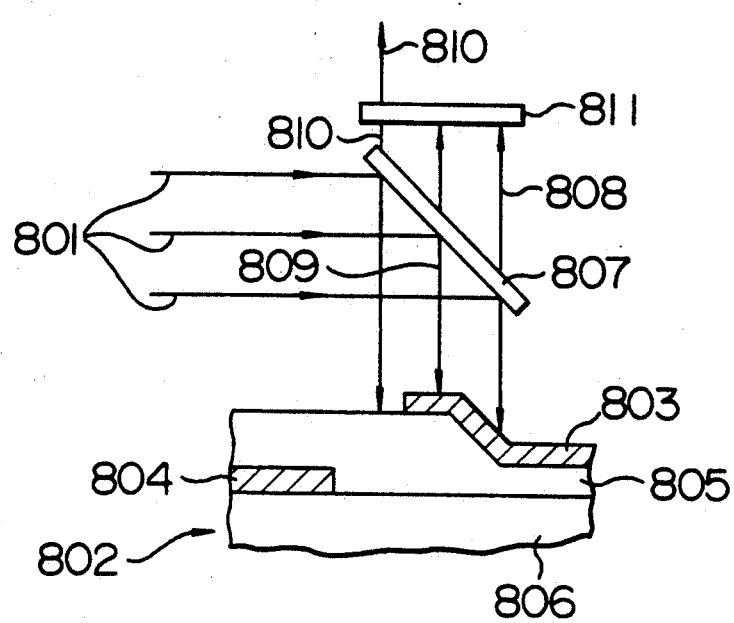
FIG. 26 shows still another example of a method for visualizing the uppermost circuit conductor pattern layer.

Now, method for visualizing an uppermost conductor pattern layer in the course of producing thin film multilayer substrate according to third type of embodiment of the invention is explained referring to FIG. 26, where fluorescence from the insulating resin layer is utilized. In this embodiment, excitation light beam 801 having a wavelength of 436 nm for example is irradiated for illumination on a surface of the substrate 802 having conductor pattern layers 803, 804 and dielectric resin layers 805, 806 through a half mirror 807. The reflection beam 808 from the surface of the uppermost conductor pattern layer 803, the reflection beam 80 from the exposed surface of the resin layer 805, and the fluorescent beam 810 from the resin layer 805 due to the fluorescence caused by the excitation beam 801 are made incident on a filter 811 designed to pass therethrough only the light of wavelengths in the range of fluorescence. Thus, only the fluorescent beam 810 from the exposed region of the resin layer 805 is passed through the filter 811 to be received by a detecting device or image-forming device such as a TV-camera. Because fluorescent beam is not emitted from the conductor pattern 803, the uppermost conductor pattern layer 803 is viewed dark, while the exposed surface of the resin layer 805 is viewed bright, thereby enabling to visualize only the uppermost conductor pattern layer 803.

Figure 27:
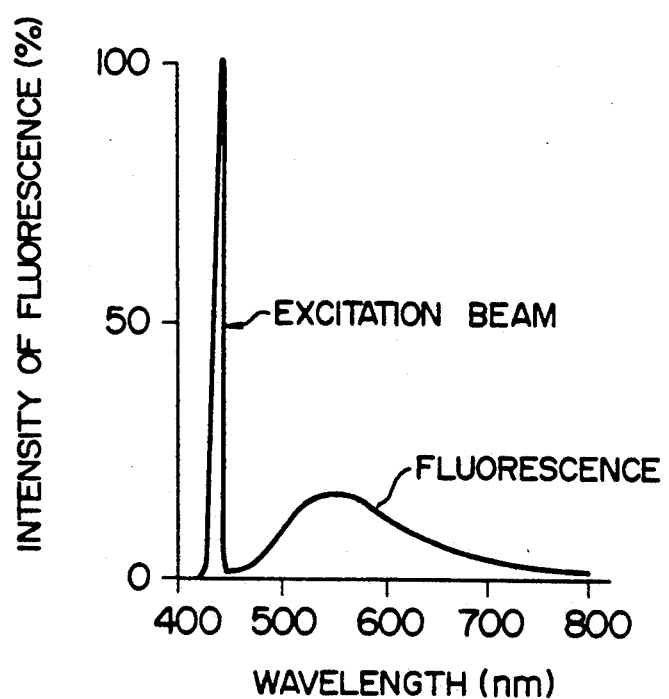
FIG. 27 is a graph showing relationship intensity of a fluorescence with an excitation beam in terms of the wavelengths thereof.

FIG. 27 is a graph showing a spectroscopic characteristics of fluorescence from polyimide type resin when excitation beam of 436 nm in wavelength is irradiated on the polyimide type resin, as an example to be applied to the embodiment of FIG. 26. In this case, for example, if only the light beam of wavelength greater than or equal to 480 nm is detected through the filter or the like, the fluorescent beam can be selectively detected.

This third type of embodiment is available so long as the conductor pattern does not emit the fluorescence and the dielectric layer emit the fluorescence. The conductor pattern layer may be made from Al, Cu or the like. The dielectric or insulating layer may be made of resin such as polyimide type resin.

Although the present invention has been fully explained by way of examples, it is apparent that the present invention is not limited to the specific embodiments but it is possible to make a variety of modifications within a scope of the claims based on the spirit of the invention.

What is claimed is:

1. A method of producing a thin film multilayer substrate, having a base substrate, a plurality of circuit conductor pattern layers superposed thereon and dielectric layers, each of the dielectric layers being interposed between portions of adjacent conductor pattern layers, by depositing layer on layer, comprising the steps of:

detecting a pattern of one of said conductor pattern layers at a time when said one of said conductor pattern layers has been newly formed at least on said base substrate and before depositing the dielectric layer thereon;
   inspecting for an absence or presence of a faulty portion in said one of said conductor pattern layers and determining a position of the faulty portion upon inspection of the presence of the faulty portion;
   repairing the faulty portion in said one of said conductor pattern layers in accordance with data of the determined position of the faulty portion; and
   subsequently depositing the dielectric layer and a further one of said conductor pattern layers on the repaired one of said conductor pattern layers;
   wherein the step of detecting a pattern comprises optically detecting the pattern by projecting one of a visible and ultraviolet light having a wavelength region so that a detected intensity of light reflected from said one of said conductor pattern layers is different from a detected intensity of light reflected from an exposed dielectric layer,
   wherein the step of optically detecting the pattern of said one of said conductor pattern layers includes detecting at least one of a regularly reflected light and a scattered light from said one of said conductor pattern layers.

2. The method according to claim 1, further comprising the step of forming a thin film resistor on the dielectric layer and forming an upper one of said conductor pattern layers.

3. The method according to claim 2, wherein said thin film resistor is made from $Cr-SiO_2$.

4. The method according to claim 1, wherein the dielectric layer is made from a polyimide type organic substance.

5. The method according to claim 1, wherein said conductor pattern layer is made from aluminum.

6. A method of producing a thin film multilayer substrate, having a base substrate, a plurality of circuit conductor pattern layers superposed thereon and dielectric layers, each of the dielectric layers being interposed between portions of adjacent conductor pattern layers, by depositing layer on layer, comprising the steps of:

detecting a pattern of one of said conductor pattern layers at a time when said one of said conductor pattern layers has been newly formed at least on said base substrate and before depositing the dielectric layer thereon;
   inspecting for an absence or presence of a faulty portion in said one of said conductor pattern layers and determining a position of the faulty portion upon inspection of the presence of the faulty portion;
   repairing the faulty portion in said one of said conductor pattern layers in accordance with data of the determined position of the faulty portion; and
   subsequently depositing the dielectric layer and a further one of said conductor pattern layers on the repaired one of said conductor pattern layers;
   wherein the step of detecting a pattern comprises optically detecting the pattern by projecting one of a visible and ultraviolet light having a wavelength region so that a detected intensity of light reflected from said one of said conductor pattern layers is different from a detected intensity of light reflected from an exposed dielectric layer,
   wherein the step of optically detecting the pattern of said one of said conductor pattern layers includes projecting light on said one of said conductor pattern layers and an exposed surface of the dielectric layer from multiple directions, and detecting the reflected light from said one of said conductor pattern layers.

7. The method according to claim 6, further comprising the step of forming a thin film resistor on the dielectric layer and forming an upper one of said conductor pattern layers.

8. The method according to claim 6, wherein the dielectric layer is made from a polyimide type organic substance.

9. The method according to claim 6, wherein said conductor pattern layer is made from aluminum.

10. A method for optically detecting an uppermost circuit conductor pattern layer of a plurality of circuit conductor pattern layers superposed through dielectric layers interposed between portions of adjacent circuit conductor pattern layers, comprising the steps of:
projecting one of a visible and ultraviolet illumination light onto an exposed surface of the uppermost conductor pattern layer and an exposed surface of one of the dielectric layers from multiple directions, and
detecting reflected light having a wavelength so that an intensity of light reflected from the uppermost conductor pattern layer is different from an intensity of light reflected from the one of the dielectric layers.

11. A method for detecting a conductor pattern layer, according to claim 10, wherein the projected illumination light and the detected reflected light are each linearly polarized, a polarization direction of the detected reflected light being perpendicular to a polarization direction of the projected illumination light.

12. The method according to claim 11, wherein said conductor pattern layers are made from aluminum.

13. The method according to claim 11, wherein said dielectric layers interposed between the conductor pattern layers are made from a polyimide type organic substance.

14. The method according to claim 10, wherein the step of projecting illumination light includes obliquely projecting the illumination light from an entire circumference of exposed surfaces onto said layers.

15. A method for producing a thin film multilayer substrate structure, comprising the steps of:
(a) producing a first thin film multilayer substrate including
 (i) forming a first thin film conductor pattern layer on a substrate,
 (ii) forming a first insulating layer having a first through-hole for electrical connection on the first thin film conductor pattern layer, and
 (iii) forming a second thin film conductor pattern layer having a flat portion and an inclined portion on the first insulating layer and which is electrically connected with the first thin film conductor pattern layer through the first through-hole;
(b) projecting light onto a surface of the first thin film multilayer substrate from light projection means at least in directions oblique relative to a principal surface of the first thin film multilayer substrate and from a circumference thereof so as to effect scanning relative thereto in two directions so that an intensity of light reflected by a surface of the inclined portion of the second thin film conductor pattern layer is substantially the same as an intensity of light reflected by a surface of the flat portion of the second thin film conductor pattern layer and so that each of intensities of light reflected by the first thin film conductor pattern layer and by the first insulating layer are lower than each of the intensities of the light reflected by the inclined and flat portions of the second thin film conductor pattern layer,
 (ii) detecting light reflected from the surface of the second thin film conductor pattern layer by optical detecting means including a transducer element for obtaining an optical image of the second thin film conductor pattern layer and providing a picture signal of the second thin film conductor pattern layer,
 (iii) comparing the picture signal of the second thin film conductor pattern layer with a reference picture signal corresponding to a standard second thin film conductor pattern layer so as to inspect for presence or absence of a fault in the second thin film conductor pattern and to determine a position of the fault upon inspection of a fault presence, and
 (iv) positioning the first thin film multilayer based on the determined position of the fault if present, and locally depositing of the fault if present, and locally depositing thin film conductor material to repair the fault, or irradiating an energy beam on the fault for removing material of the fault to repair the fault; and
(c) subsequently, producing a second thin film multilayer substrate including
 (i) forming a second insulating layer having a second through-hole for electrical connection, on the repaired second thin film conductor pattern layer, and
 (ii) forming a third thin film conductor pattern layer on the second insulating layer and which is electrically connected with the second thin film conductor pattern layer through the second through-hole.

16. The method according to claim 15, wherein the light of step (b)(i) has a wavelength so that reflectivity of the light from the surface of the second thin film conductor pattern layer is high.

17. The method according to claim 16, wherein the detection of the light reflected from the second thin film conductor pattern layer is carried out by collecting light scattered at the second thin film wiring pattern layer with the optical detecting means.

18. The method according to claim 16, wherein the light projected, at the step (b)(i) has a wavelength so that reflectivity of the light at the second thin film conductor pattern layer is high in a direction generally normal to the flat portion of the second thin film conductor pattern layer.

19. The method according to claim 15, wherein the light projected at the step (b)(i) is a polarized laser beam and the detection of light reflected from the surface of the second thin film conductor layer by the optical detecting means is carried out so as to avoid receiving the light reflected as a stepped portion of the first insulating layer.

20. The method according to claim 15, wherein the detection of the light reflected from the second thin film conductor pattern layer is carried out by collecting light scattered at the second thin film conductor pattern layer with the optical detecting means.

21. The method according to claim 15, further comprising the steps of:
(d) further inspecting including
 (i) projecting a light onto a surface of the second thin film multilayer substrate intermediate structure from light projection means at least in directions oblique relative to a principal surface of the second thin film multilayer substrate and from a circumference thereof so as to effect scanning relative thereto in two directions so that an intensity of light reflected by a surface of an inclined portion of the third thin film wiring conductor pattern layer is substantially the same as an intensity of light reflected by a surface of a flat portion of the third thin film conductor pattern layer and so that each of intensities of light reflected by the second thin film conductor pattern layer and by the second insulating layer are lower than each of the intensities of the light reflected by the inclined and flat portions of the third thin film conductor pattern layer, (ii) detecting light reflected from the surface of the third thin film conductor pattern layer, the optical detecting means including the transducer element for obtaining an optical image of the third thin film conductor pattern layer and providing a picture signal of the third thin film conductor pattern layer, (iii) comparing the picture signal of the third thin film conductor pattern layer with a reference picture signal corresponding to a standard third thin film conductor pattern layer, a pattern of which is different from a pattern of the second thin film conductor pattern layer, to inspect for presence or absence of a fault in the third thin film conductor pattern and to determine a position of the fault upon inspection of a fault presence, and (iv) positioning the second thin film multilayer substrate based on the determined position of the fault if present, and locally depositing thin film conductor material to repair the fault, or irradiating an energy beam on the fault for removing material of the fault to repair the fault; and (e) subsequently, producing a third thin film multilayer substrate including (i) forming a third insulating layer, having a third through-hole for electrical connection, on the repaired third thin film conductor pattern layer, and (ii) forming a fourth thin film conductor pattern layer, on the third insulating layer, and which is electrically connected with the third thin film conductor pattern layer through the third through-hole.

22. A method for producing a thin film multilayer substrate structure, comprising the steps of:

(a) producing a first thin film multilayer substrate including (i) forming a first thin film conductor pattern layer on a substrate, (ii) forming a first insulating layer having a first through-hole for electrical connection on the first thin film conductor pattern layer, and (iii) forming a second thin film conductor pattern layer having a flat portion and an inclined portion, on the first insulating layer, and which is electrically connected with the first thin film conductor pattern layer through the first through-hole;

(b) inspecting including (i) projecting an excitation light, capable of generating fluorescence from the first insulating layer, onto the first thin film multilayer substrate from a light projection means so as to effect scanning relative thereto in two directions, (ii) detecting fluorescence from the first insulating layer by optical detecting means including a transducer element for obtaining an optical image of the second thin film conductor pattern layer and providing a picture signal of the second thin film conductor pattern layer, (iii) comparing the picture signal of the second thin film conductor pattern layer with a reference picture signal corresponding to a standard second thin film conductor pattern layer to inspect for presence or absence of a fault in the second thin film conductor pattern and to determine a position of the fault upon inspection of a fault presence, and (iv) positioning the first thin film multi-layer substrate based on the determined position of the fault if present, and locally depositing thin film conductor material to repair the fault, or irradiating an energy beam on the fault for removing material of the fault to repair the fault; and (c) subsequently, producing a second thin film multilayer substrate including (i) forming a second insulating layer, having a second through-hole for electrical connection, on the repaired second thin film conductor pattern layer, and (ii) forming a third thin film conductor pattern layer on the second insulating layer and which is electrically connected with the second thin film wiring pattern layer through the second through-hole.

23. The method according to claim 22, further comprising the steps of (d) further inspecting including (i) projecting an excitation light, capable of generating fluorescence from the second insulating layer, onto a surface of the second thin film multilayer substrate from a light projection means so as to effect scanning relative thereto in two directions, (ii) detecting fluorescence from the second insulating layer by means of optical detecting means including a transducer element for obtaining an optical image of the third thin film conductor pattern layer and providing a picture signal of the third thin film conductor pattern layer, (iii) comparing the picture signal of the third thin film conductor pattern layer with a reference picture signal corresponding to a standard third thin film conductor pattern layer, a pattern of which is different from a pattern of the second thin film conductor pattern layer, to inspect for presence or absence of a fault in the third thin film conductor pattern and to determine a position of the fault upon inspection of a fault presence, and (iv) positioning the second thin film multilayer substrate based on the determined position of the fault if present, and locally depositing thin film conductor material to repair the fault, or irradiating an energy beam on the fault for removing material of the fault to repair the fault; and (e) subsequently, producing a third thin film multilayer substrate including (i) forming a third insulating layer, having a third through-hole for electrical connection, on the repaired third thin film conductor pattern layer, and (ii) forming a fourth thin film conductor pattern layer on the third insulating layer and which is electrically connected with the third thin film conductor pattern layer through the third through-hole.

* * * * *